United States Patent
Endrici

(12) 
(10) Patent No.: US 6,291,534 B1
(45) Date of Patent: Sep. 18, 2001

(54) CHEMICAL ENTITY (ENDIPALENE) IN THE TREATMENT OF PSORIASIS

(76) Inventor: Giorgio Endrici, Via Brescia 2, 38100 Trento (IT)

(*) Notice: Subject to any disclaimer, the term of this patent is extended or adjusted under 35 U.S.C. 154(b) by 0 days.

(21) Appl. No.: 09/485,700

(22) PCT Filed: Aug. 27, 1998

(86) PCT No.: PCT/IT98/00236
  § 371 Date: May 25, 2000
  § 102(e) Date: May 25, 2000

(87) PCT Pub. No.: WO99/11249
  PCT Pub. Date: Mar. 11, 1999

(30) Foreign Application Priority Data

Aug. 29, 1997 (IT) ................................. 97A000008

(51) Int. Cl.$^7$ ................................................ A61K 31/03
(52) U.S. Cl. .......................................................... 514/753
(58) Field of Search ............................................... 514/753

(56) References Cited

U.S. PATENT DOCUMENTS

| | | | | |
|---|---|---|---|---|
| 5,712,312 | * | 1/1998 | Langlois et al. | 514/585 |
| 6,156,790 | * | 12/2000 | Posner et al. | 514/450 |
| 6,160,004 | * | 12/2000 | Posner et al. | 514/450 |

OTHER PUBLICATIONS

N. Motoyama et al., Pesticide Biochemistry and Physiology, vol. 9 (1978), pp. 255–262; "Endogenous Inhibitors of Glutathione S–Transferase in House Flies".

D. G. Batt, Progress in Medicinal Chemistry, vol. 29 (1992), pp. 1–63; "5–Lipoxygenase Inhibitors and their Anti–inflammatory Activities".

A. K. Black et al., J. of Investigative Dermatology, vol. 95, No. 1, Jul. 1990, pp. 50–54; "Pharmacologic and Clinical Effects of Lonapalene (RS 43179), a 5–Lipoxygenase Inhibitor, in Psoriasis".

G. H. Jones et al., J. Med. Chem., vol. 29, No. 8 (1986), pp. 1504–1511; "Topical Nonsteroidal Antipsoriatic Agents. 1. 1,2,3,4–Tetraoxygenated Naphthalene Derivatives".

P. A. Lehman, Pharmaceutical Research, vol. 9, No. 9 (1992), pp. 1145–1151; "Percutaneous Absorption and Metabolism of Lonapalene in Psoriatic Skin".

M. C. Venuti et al., J. Med. Chem., vol. 31, No. 11 (1988), pp. 2132–2136; "Topical Nonsteroidal Antipsoriatic Agents. 2. 2,3,–(Alkylidenedioxy)naphthalene Analogues of Lonapalene".

* cited by examiner

Primary Examiner—William R. A. Jarvis
Assistant Examiner—Vickie Kim
(74) Attorney, Agent, or Firm—Arent Fox Kintner Plotkin & Kahn PLLC

(57) ABSTRACT

In the literature, a correlation between the inhibition of 5-lipoxygenase and anti-inflammatory and immunomodulatory activity sufficient to effectively treat psoriasis, is known. It seems that, in particular, the excellent results can be obtained with lonapalene (6-chloro-2,3-dimethoxynaphthalendioldiacetate). However, the clinical use of lonapalene has not been successful most likely due to the significant number of side effects. With these considerations, after various studies, we have identified a molecule which we have patented with the name of endipalene, which seems to guarantee notable therapeutic results without side effects.

2 Claims, 1 Drawing Sheet

LONAPALENE 2, 6-DIMETHOXYNAPTHALENE $C_{10}H_6(OCH_3)_2$ $C_{12}H_{12}O_2$ 2, 7-DIMETHOXYNAPTHALENE $C_{10}H_6(OCH_3)_2$ $C_{12}H_{12}O_2$

ENDIPALENE

CHEMICAL ENTITY (ENDIPALENE) IN THE TREATMENT OF PSORIASIS

This application is a 371 of PCT/IT98/00236 filed Aug. 27, 1998.

TECHNICAL FIELD

My invention relates to the field of molecules with two aromatic condensed rings (naphtalenic rings) characterized by a good activity against inflammation through inhibitory actions in one or more passages of the "fall" of the arachidonic acid.

BACKGROUND ART

From the beginning of the nineties in the medical literature lots of studies appeared about a molecule patented as lonapalene (drawings, FIG. 1) with a great power against inflammation of the skin Lonapalene (6-chloro-2,3-dimethoxynaphthalendioldiacetate) has a statistically significant reduction in the levels of material similar or identical to the chemoattractant arachidonate 5-lipoxygenase product, leukotriene B4 (Black A. K., LAMP R D., Malled A T., Cunningham F M., Hofbauer M., Greaves M W.; PHARMACOLOGIC AND CLINICAL EFFECTS OF LONAPALENE-RS43-179-A 5-LIPOXYGENASE INHIBITOR IN PSORIASIS; JOURNAL OF INVESTIGATIVE DERMATOLOGY 95(1):50–4, 1990 July) A wide variety of agents have been reported as 5-lipooxygenase inhibitors. The majority of the series appear to be lipophilic reducing agents, including phenols, partially saturated.

Aromatics and compounds containing heteroatom-heteroatom bonds are the-same. Many of these are not selective 5-LO inhibitors.

In vivo sistemic activity for many of these has been in general, disappointing, probably because of poor bioavailability caused by lipophilicity and metabolic instability (oxidation and conjugation of phenolic compounds). However, topically a number of agents have shown promise for skin inflammation, and best of all, lonapalene; (Batt D G., 5-LIPOXYGENASE INHIBITORS AND THEIR ANTI-INFLAMMATORY ACTIVITIES, PROGRESS IN MEDICINAL CHEMISTRY, 29:1–63, 1992).

Unfortunately, the clinical utilisation of lonapalene wasn't successful, probably because of the remarkable side effects. Lots of attempts have been made to find other topical nonsteroidal antipsoriatic agents analogues of lonapalene, without any success;(Venuti M C., Loe B E., Jones G H., Young G M., TOPICAL NONSTEROIDAL AN TIPSORIATIC AGENTS. 2.2,3-ALKYLIDENEDIOXYNAPHTALENE ANA LOGUES OF LONAPALENE, JOURNAL OF MEDICINAL CHEMISTRY, 31(11):2132–6, 1988 November). (Jones G H., Venuti M C., YOUNG J M., Murthy D V., Loe B E., Simpson R A., Berks A H., Spires D A., Malonej P J., Kruseman M., et al., TOPICAL NON STEROIDAL ANTIPSORIATIC AGENTS. 1.1,2,3,4,-TETRAOXYGENATED NAPHTALENE DERIVATIVES, JOURNAL OF MEDICINAL CHEMISTRY, 29(8):1504–11, 1986 August).

DISCLOSURE OF INVENTION

Considering what I reported before, my attention turned to find out a molecule as efficacious as lonapalene avoiding the negative side effects.

After a first screening which led me to select molecules without halogens, a molecule has been found:

2,6 or 2,7-dimethoxynaphtalene that I patented with the name of ENDIPALENE.

Endipalene seems to have the same action mechanism of lonapalene excluding remarkable side effects.

BRIEF DESCRIPTION OF DRAWINGS

The enclosed drawings show the structural formulas of lonapalene (FIG. 1) and endipalene (FIG. 2).

BEST MODE FOR CARRYING OUT THE INVENTION

Figure 1:
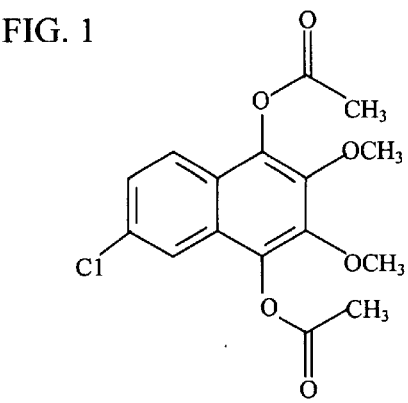
Figure 2:
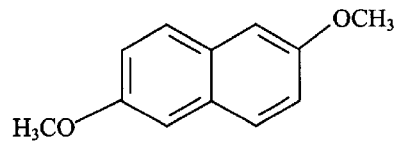
Figure 2:
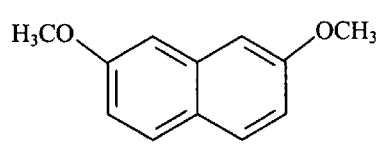

I think that endipalene should be used topically, with a concentration between 1% or 2%.

We need to continue studying in order to confirm the selective action mechanism (inhibitor of 5-LO), to check skin absorption, pharmacokinetics, metabolism. We should also confirm the absence of side effects and verify the results after long time.

INDUSTRIAL APPLICABILITY

If one considers that psoriasis afflicts 2% of the population in North Europe and an equal portion of the Caucasians in the USA and that more than 91% of patients with psoriasis have a relative or first or second degree afflicted with the same disease, it is evident that there is a significant possibility to get success in the field of, if research confirm the positive results.

What is claimed is:

1. A method for treating psoriasis comprising administering to a patient suffering form psoriasis an effective amount of a pharmaceutical composition comprising an effective amount of endipalene and a pharmaceutically acceptable carrier.

2. A method for treating psoriasis comprising administering to a patient suffering from psoriasis an effective amount of endipalene.

* * * * *